United States Patent [19]

Hauser

[11] 4,270,039
[45] May 26, 1981

[54] HEATING UNIT WITH INDICATOR FOR DISINFECTING SOFT LENSES, OR THE LIKE

[75] Inventor: Stephen G. Hauser, Tarzana, Calif.

[73] Assignee: Rincon Industries, Inc., Los Angeles, Calif.

[21] Appl. No.: 67,478

[22] Filed: Aug. 17, 1979

[51] Int. Cl.³ .......................................... F27D 11/02
[52] U.S. Cl. .......................... 219/439; 116/DIG. 16;
126/388; 219/385; 219/430; 219/441; 219/521;
422/56
[58] Field of Search ............... 219/328, 385, 430, 438,
219/439, 441, 442, 521; 116/202, 217, 117,
DIG. 16, 206; 422/56, 58, 87, 307; 126/388

[56] References Cited

U.S. PATENT DOCUMENTS

| 3,130,288 | 4/1964 | Monaco et al. | 219/385 |
| 3,247,360 | 4/1966 | Ponder | 219/436 |
| 3,801,278 | 4/1974 | Wagner et al. | 219/439 X |
| 3,998,590 | 12/1976 | Glorieux | 422/117 |
| 4,158,126 | 6/1979 | Seitz | 219/439 |
| 4,178,499 | 12/1979 | Bowen | 219/439 |

*Primary Examiner*—Volodymyr Y. Mayewsky
*Attorney, Agent, or Firm*—Keith D. Beecher

[57] ABSTRACT

An indicator is provided for a heating unit, which heating unit may be used as a soft contact lens disinfecting means, and which includes wax as a heat transfer medium, as a temperature stabilization means, and as a heat storage medium. In accordance with the present invention, an indicator assembly for such a heating unit is provided, and which indicates to the user when the unit is energized, when the unit has reached its proper operating temperature, and when the unit has completed a heating, disinfecting cycle. The indicator assembly of the invention is in the form of a hollow plug which extends into the interior of the heating unit, and which itself is filled with wax. The plug has an indicator disc, which may be of a bright color such as red, attached to its bottom to be visible through the wax in the plug and through the transparent cover of the plug only when the wax within the plug is in a transparent molten state. Since the plug is in contact with the wax in the heating unit itself, the fact that the wax in the plug has reached a transparent molten state is an indication that the wax within the heating unit is also in a molten state, and that the heating unit has reached its operating temperature. The plug also includes a light pipe which extends through it, and which enables the user to see an electric light bulb which is buried in the wax within the interior of the heating unit, and which is energized when the heating unit is energized.

4 Claims, 2 Drawing Figures

HEATING UNIT WITH INDICATOR FOR DISINFECTING SOFT LENSES, OR THE LIKE

RELATED COPENDING APPLICATIONS

Ser. No. 835,420—Bowen, filed Sept. 21, 1977, which has now issued as U.S. Pat. No. 4,178,499.

BACKGROUND

It is necessary to produce periodically an essentially disinfected condition in soft contact lenses so that bacterial organisms or their by-products will not cause harm to the wearer's eyes. Since the soft lens material is permeable to liquids, soaking the lens in strong germicidal solutions will result in the lens becoming impregnated with the solution, and this can lead to irritation to the user's eyes when the lens is worn. In general, it has been found difficult, if not impossible, to disinfect soft lens by treatment with chemical or biochemical solutions which will not cause eye irritation to at least some percentage of the wearers.

As an alternate means for producing the desired disinfected condition in the soft lens, heat has been used in the past. Since the lens must be kept immersed in physiologically normal saline solutions, or its equivalent, when it is not being worn, to prevent the lens material from drying out, heat is generally applied by first placing the lens in a saline solution in a container, and then placing the container in a heating unit.

The heating unit must raise the temperature of the saline solution and immersed lens in the container to the required temperature, hold the lens at or above this temperature for the required time, and then allow the lens to cool to ambient temperature. Typical values of the time and temperature deemed suitable for producing the disinfected condition require that the lens to be maintained at or about 80° C., for a period of 10 minutes or more. Since aging of the lens material is accelerated by excessive temperatures and/or by extended time at elevated temperatures, it is desirable that the heating unit be controlled so that excessive temperatures, or excessive time at elevated temperatures, will not shorten the life of the lens.

It is also desirable that the lens user be able to check periodically on the proper operation of the heating unit to insure that the unit has reached the desired temperature. An indicator light on a typical prior art electrical heating unit only tells the user that the unit has been turned on. The light may well function normally even if the heating element in the unit is defective and the lens has not reached the proper disinfecting temperature.

The Bowen U.S. Pat. No. 4,178,499 referred to above provides a simple and inexpensive indicator assembly for use in a heating unit of the type disclosed in Seitz U.S. Pat. No. 4,158,126, by which the user may observe when the proper temperature has been reached after the unit has been energized. The indicator disclosed in the Bowen patent comprises an indicator strip which is mounted within the interior of the heating unit, and which is displaced from a window in the wall of the unit. The strip is not visible through the window in the unit so long as the wax within the unit is in a solid opaque state. However, when the wax is heated to its molten state, it becomes transparent, and the indicator is then visible. The present invention provides a simple and inexpensive indicator which operates on the same principle as the indicator of the Bowen patent, but which is housed in a separate plug so as to be easier and less expensive to produce.

DETAILED DESCRIPTION OF THE ILLUSTRATED EMBODIMENT

Figure 1:
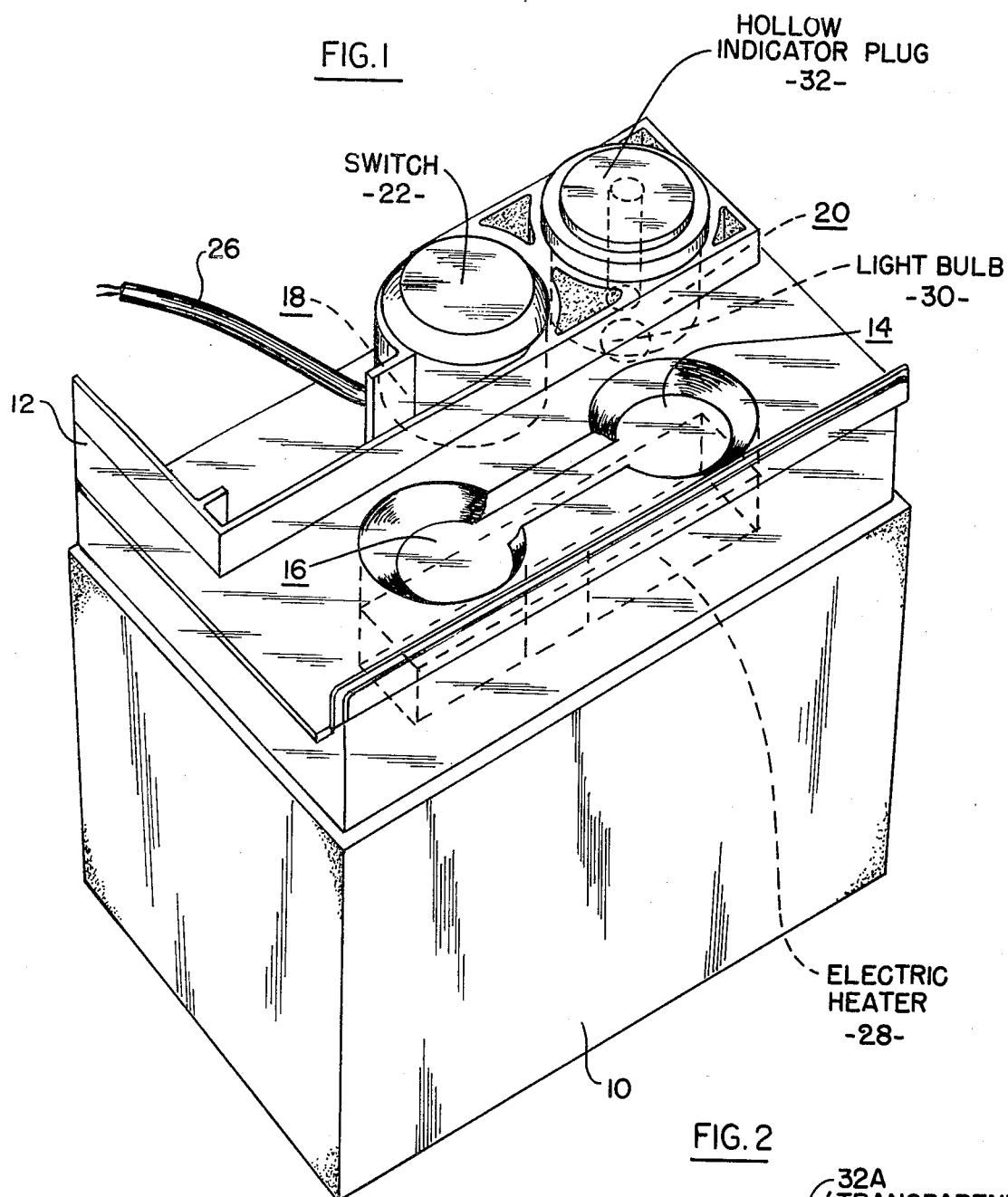
FIG. 1 is a perspective representation of a heating unit, with its cover removed, and including an indicator assembly constructed in accordance with one embodiment of the invention.

The heater unit of FIG. 1 includes a bowl 10 which may be formed of any appropriate plastic material, such as high operating temperature grade polycarbonate. An incubator 12 is mounted on top of, and is sealed to the bowl 10, and it likewise may be formed of high temperature grade plastic, such as polycarbonate. The incubator extends down into the bowl. Both the bowl and incubator may be mounted in an appropriate housing, such as shown and described in Sietz U.S. Pat. No. 4,158,126.

The incubator 12 is formed to define two wells 14 and 16 of suitable dimensions to accept the maximum size lens case to be used as containers for soft contact lenses during the heating/disinfecting operation of the unit. The incubator 14 is also shaped to define a switch cavity 18 and a wax fill hole 20. An appropriate pushbutton thermostatic switch 22 is mounted in the switch cavity 18. An electric cord 26 is connected through the switch 22 to an electric heater 28 which is mounted on the underside of the wells 14, 16.

The bowl 10 is filled with wax through the fill hole 20, and when electric heater 28 is energized, the wax is heated to a molten state, during which the heat from the wax is transferred to the interior of the wells 14, 16, as described in the patent. An electric light bulb 30 is embedded in the wax adjacent to the fill hole 20, and it is energized when the switch 22 is operated to energize electric heater 28.

All of the foregoing elements and other elements of the unit, with the exception of light bulb 30, including an appropriate electrical circuit for energizing the unit, are fully illustrated and described in the Bowen and Seitz patents referred to above, and it is believed necessary for these elements to be shown or described in detail in the present specification.

Figure 2:
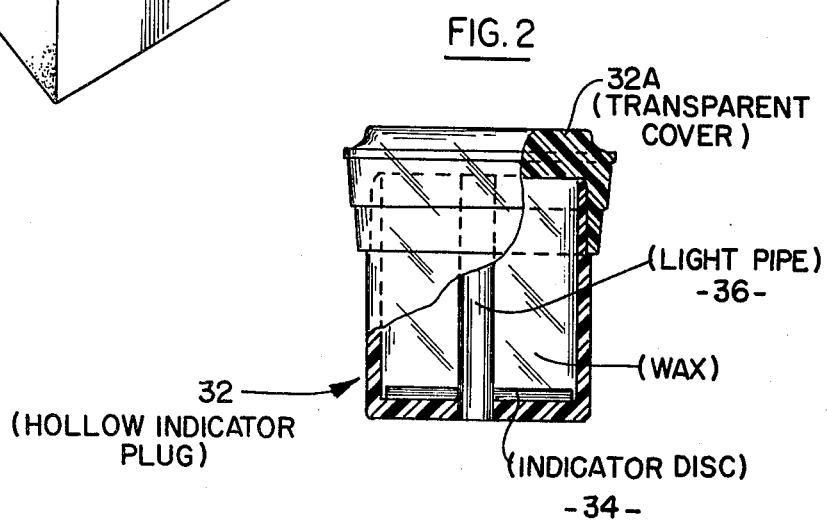
FIG. 2 is a view, partly in section, of the indicator assembly of FIG. 1, which, in accordance with the invention, is housed in a separate plug which is used to enclose the hole in the unit of FIG. 1 through which wax is introduced to the interior thereof.

In accordance with the present invention, the fill hole 20 is closed by a hollow indicator plug 32. The indicator plug 32, as best shown in FIG. 2, is also filled with wax, and it includes a transparent cover 32A. An indicator disc 34 is mounted on the bottom of the hollow plug 32. The indicator disc may be any appropriate color, such as red. A light pipe 36 extends along the longitudinal axis of the hollow plug 32 and through indicator disc 34 to the bottom of plug 32. The portion of the bottom of plug 32 adjacent to the lower end of the light pipe may be made transparent, or the light plug 36 may extend through the bottom of the plug, so that ight bulb 38 may be observed through the light pipe and through the transparent cover 32A of the plug when it is energized, so as to inform the user that the switch 22 has been operated to energize the electric heater 28.

When the wax within the interior of bowl 10 reaches a molten state, the heat from that wax is transmitted to the interior of the hollow plug 32, so that the wax in the plug 32 also becomes molten, and when that occurs, the user can see the indicator disc 34 through the transparent cover 32A, and is thereby informed that the unit is in an operational state.

Specifically, during the fabrication of the unit of FIG. 1, the bowl 10 is filled with molten wax through the fill hole 20 at a temperature of approximately 100° C., to a level above the bottom of wells 14, 16, so that electric heater 28 is submerged in the molten wax, and the wells 14, 16 are surrounded by wax. The indicator plug 32 is then seated into the wax fill hole 20, and is sealed in place, preferably by ultrasonic welding, so as to provide a leak-tight container for the wax in bowl 10. The wax in bowl 10 preferably is a typical hydrocarbon paraffin wax which is readily available. The wax within the bowl 10 performs a number of functions as fully described in the Seitz patent. For example, when the unit is cold, at the start of the disinfection cycle, the wax is in a solid state, as is the wax in indicator plug 32, so that the indicator 34 is blocked from view.

As also described in detail in the Bowen and Seitz patents, when the heating unit approaches its operating temperature in the disinfection cycle, the wax within the bowl 10 melts and becomes a clear liquid, as does the wax within the plug 32. The indicator 32 can now be viewed through the transparent cover 32A, which provides a positive indication to the user that the proper disinfection temperature has been reached. When the proper temperature has been reached, thermostatic switch 22 snaps off automatically and the unit begins to cool down. As the unit cools down, the wax within the bowl 10 returns to its solid state, and the wax in the plug 32 also returns to its solid white opaque state, and the indicator 34 is no longer visible through the transparent cover 32A, so that the user has a positive indication that the disinfection cycle has been completed, and that the lenses have been properly disinfected.

As also described in detail in the Seitz patent, the wax within bowl 10 also acts as a heat transfer medium. When the unit is cold, and when it is energized by depressing thermostatic switch 22 in cavity 18, the heating element 28 begins to heat up. This action causes the solid wax within the bowl adjacent to the heating element to melt, and the melted liquid wax then begins to circulate by convection. The hot wax tends to rise, carrying heat to the unmelted wax towards the top of the unit by convection currents, as well as to the wells of the lens holder wells 14, 16. After substantially all of the wax within the bowl has been melted, no further heat input is required to supply the heat of fusion in melting the wax, and the temperature of the liquid wax within the bowl will begin to rise above the melting temperature of the wax. When the molten wax reaches a predetermined temperature above its melting temperature, the thermostatic switch 22 in cavity 18 reaches its snap-off point. At that time, power is removed from the heating element 28, and the unit begins to cool down.

As also described in detail in the Seitz patent, when the thermostatic switch snaps off, it remains off until it is manually re-set. In this way, a disinfecting cycle for the lenses within the wells 14, 16 is initiated merely by actuating switch 22. When switch 22 is actuated to energize the heating unit, light bulb 30 is energized, and can be observed through the indicator plug 32. The wax within the bowl 10, in time, reaches its molten state, as does the wax within the plug 32. When that occurs, the indicator disc 34 may be observed so that the user knows that the unit is carrying out the disinfecting cycle. In due course, the switch 22 will automatically switch off, and the user will be informed that the disinfecting cycle is completed, when he can no longer see indicator 34 through the transparent cover 32A of plug 32.

The plug 32, therefore, serves to seal off the wax fill hole 20 as a final hermetic operaton, and thereby serves to maintain the wax within the bowl 10. The plug also contains wax which may be the same or different from the specific wax contained within the bowl, and which may have a selected percentage of mineral oil added to it (up to 20% by volume, for example). The combination of the mineral oil and selected wax within the plug 32 is such to dictate a point of phase change of the wax from solid and opaque to liquid and clear at a lower temperature than the wax within the bowl. When the proper proportions and selections are made, then as heater 28 heats, the indicator disc 34 at the bottom of the plug 32 becomes visible through the transparent cover 32A at the heater's peak temperature, and just as the thermostatic switch 22 switches off. On cool-down, the indicator 34 is visible through the transparent cover 32A until the temperature of the wax within the bowl 10 drops to approximately 42° C., at which time the wax within the plug 32 becomes solid and opaque, so that the indicator 34 is no longer visible. When that occurs, the user is made aware of the fact that the disinfecting cycle has been completed, and that the lenses may be removed from the wells 14, 16.

It will be appreciated that although a particular embodiment of the invention has been shown and described, modifications may be made. It is intended in the following claims to cover all modifications which come within the true spirit and scope of the invention.

What is claimed is:

1. In an electrically energized heating unit which comprises a bowl having an open top, an incubator supported in and covering the open top of the bowl and including at least one well extending into the bowl, electrical heating means mounted in the bowl, and wax contained in the bowl to be heated from a solid state to a molten state by the electrical heating means when the electrical heating means is energized so as to introduce heat into the well; the combination of a hollow plug extending into said bowl and into the wax contained in said bowl, said plug containing wax which is molten and transparent when the wax in the bowl is molten and transparent, and which is solid and opaque when the wax in the bowl is solid; a transparent member mounted at the top of the plug, and an indicator member mounted at the bottom of the plug to be visible through the transparent member when the wax in the plug is in a molten state and to be invisible through the transparent member when the wax in the plug is in a solid state.

2. In the combination defined in claim 1, in which said incubator includes an opening through which wax may be introduced to the interior of the bowl, and in which said plug is mounted on said incubator and extends through said opening into the interior of the bowl and into the wax in the bowl.

3. In the combination defined in claim 1, in which said transparent member forms a top cover for the plug.

4. In the combination defined in claim 2, and which includes an electrically energized light source mounted in said bowl adjacent to the bottom of said plug, and which includes a light pipe extending in the plug from the bottom of the plug to the top of the plug and whose lower end is visible to the light source, so as to render the light source visible through the light pipe and through the transparent member when the light source is energized.

* * * * *